(12) United States Patent
Berlin et al.

(10) Patent No.: US 6,358,754 B1
(45) Date of Patent: Mar. 19, 2002

(54) (BIO)CHEMICAL REAGENT SOLID PHASES, PROCESS FOR THEIR PRODUCTION AND THEIR APPLICATIONS

(75) Inventors: Peter Berlin, Jülich; Jörg Tiller, Jena; Dieter Klemm, Weimar, all of (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 09/101,680
(22) PCT Filed: Jan. 9, 1997
(86) PCT No.: PCT/DE97/00072
  § 371 Date: Jul. 10, 1998
  § 102(e) Date: Jul. 10, 1998
(87) PCT Pub. No.: WO97/25621
  PCT Pub. Date: Jul. 17, 1997

(30) Foreign Application Priority Data

Jan. 12, 1996 (DE) .......................... 196 00 930

(51) Int. Cl.$^7$ .................. G01N 33/544; C12Q 1/26; C12N 9/02; B01D 61/00; B01D 39/00
(52) U.S. Cl. .................. 436/530; 435/25; 435/189; 210/649; 210/650; 210/651; 210/652; 210/653; 210/654; 210/655; 210/500.29; 210/500.3; 210/500.31; 210/500.32
(58) Field of Search ................ 210/634, 638, 210/644–647, 649–655, 500.29, 500.3, 500.31, 500.32; 556/419, 421; 427/245; 436/530; 435/189, 25

(56) References Cited

U.S. PATENT DOCUMENTS

| 4,273,359 A | * | 6/1981 | Scholz et al. ............... 280/740 |
| 4,486,549 A | * | 12/1984 | Matsumoto et al. .......... 521/53 |
| 4,514,506 A | * | 4/1985 | Braatz et al. ............... 436/518 |
| 5,015,387 A | | 5/1991 | Nemori et al. |

FOREIGN PATENT DOCUMENTS

DE 473097 3/1929
EP 0 131 369 A2 1/1985

OTHER PUBLICATIONS

Loudon, G.M. Organic Chemistry. 2nd Ed. Benjamin/Cummings Publishing Co., p. 760, 1988.*
Tiller et al. Biotech. Appl. Biochem. vol. 30, pp. 155–162, 1999.*
Robinson et al. Clin. Chem. vol. 31, No. 9, pp. 1449–1452, Sep. 1985.*
Pekin et al. Biotech. Bioeng. vol. 23, pp. 1907–1911, 1981.*
Immobilized Affinity Ligand Techniques, by Greg. T. Hermanson; A. Krishna Millia and Paul K. Smith, (1992) Published by Academic Press Inc.
Kodansha Scientific Books, (1978), Halsted Press, pp. 7–9, 2 through 21.
Electrochemical Biosensors; reprinted from Analytical Chemistry, (1987), 59, 933A.
Phil. Trans. R. Soc. Land. B 316, 95–106 (1987), By J.E. Frew and H.A.O. Hill, pp. 95 to 106.
Surface Electrochemistry, John O'M, Bockris, and Shahed U.M. Khan, (1993) Plenum Press, pp. xi–xxxii.
SPIE, (1994) vol. 2068, pp. 2–10.
Biosensors & Bioelectronics 9 (1994) Elsevier Science Publishers Ltd., pp. 207–216.

* cited by examiner

Primary Examiner—Padmashri Ponnaluri
Assistant Examiner—Maurie E. Garcia
(74) Attorney, Agent, or Firm—Herbert Dubno; Jonathan Myers

(57) ABSTRACT

Novel solid phase reaction supports are disclosed. The solid phase reaction supports include (a) a solid phase carrier having a multiplicity of $NH_2$ functional groups;
(b) a coupling compound covalently bonded to an $NH_2$ group of the solid phase carrier; and
(c) a receptor compound coupled to the solid phase carrier through the coupling compound.

The coupling compound is preferably ascorbic acid, dehydroascorbic acid or a diketo compound structurally similar to ascorbic acid or dehydroascorbic acid. The solid phase carrier is preferably made of cellulose.

9 Claims, 2 Drawing Sheets

(BIO)CHEMICAL REAGENT SOLID PHASES, PROCESS FOR THEIR PRODUCTION AND THEIR APPLICATIONS

FIELD OF THE INVENTION

The invention relates to (bio)chemical reagent solid phases which are comprised of a polymer or macromolecular $NH_2$-containing support compound, on which coupling structures are bound via $NH_2$ groups covalently and which is further coupled with a receptor compound and/or indicator compound and thus the receptor and/indicator compounds can be coupled to the carrier. The invention also relates to a process for producing (bio)chemical reagent solid phases and their applications.

BACKGROUND OF THE INVENTION

With (bio)chemical reagent solid phases of the afore-described type, by the coupling of receptor compounds to the carrier compound, the receptors can be immobilized. Such immobilized receptor compounds have utility in a variety of fields and have been known for a long time. A typical field of use is in biotechnology, in (bio)chemical sensors and biochemical analysis as, for example, chromatography. Of interest are special immobilized biological compounds like enzymes or immunoproteins. With these, the (enzyme) catalytic function or complementarity is used for producing and/or purifying substances or by complementarity is used analytically for detection of analyte materials and for signal processes.

With respect to the immobilization process and the composition of reagent solid phases, there is an enormous variation described in the technical literature. They are produced above all by the modification:

of the structure of the carrier compound as, for example, macromolecular carriers of an organic or inorganic nature like collagens, dextrans or porous glass and the like and polymeric carriers of polar and nonpolar nature like polyamides, polyurethanes or polystyrenes, polyethylenes or the like;

of an immobilizing kind or utilizing an immobilization process as for example immersion or adsorption electrostatic or covalent fixation, for example, via so-called bifunctional coupling compounds typically by means of glutaricdialdehyde or the like or via the use of conventional synthesis reaction, e.g. substitution reactions, diazotizing reactions or the like;

of the receptor compound, for example, biocompounds like enzymes (oxide reductases, proteases or the like or immunoproteins (antibodies) or organic receptor compounds like crown ethers for ions or the like.

See Hermanson, G. T. et al (Ed.): Immobilized Affinity Ligand Technics, Academic Press, 1992 or Chibatu, I. (Ed.): Immobilized Enzymes, Research and Development, Kodanska Scientific Books, 1978).

Especially for the immobilization of biocompounds like enzymes or immunoproteins, polysaccharides, especially cellulose can be used as the carrier compound. For all of the important immobilization categories like carrier inclusion, ion association covalent bonding a multiplicity of variations have been found also with respect to the biocompounds which are incorporated. Table 1, assembles a collection of selected possibilities (compare the above-cited Hermanson, G. T. et al).

TABLE 1

Example of Enzyme-Immobilizations on Cellulose Derivatives

| Cellulose Derivative | Immobilization type | Enzyme Example |
|---|---|---|
| Butylacetatcellulose | Carrier inclusion | Urease, etc. |
| Nitrocellulose | Carrier inclusion | Lactase, Asparaginase, etc. |
| Collodium | Carrier inclusion | Lactase, Urease etc. |
| DEAE-Cellulose | Ion-inclusion | Catalase, Invertase, Pepsin, etc. |
| TEAE-Cellulose | Ion inclusion | Aspartase, etc. |
| Covalent Bonding To: | | |
| p-Aminobenzylcellulose | Diazo-Reaction | Catalase, Invertase, Pepsin, Aspartase etc. |
| p-Aminobenzoylcellulose | Diazo-Reaction | Trypsin, Chymotrypsin, etc. |
| Bromcyan-activated Cellulose | Bromcyan activation | Xanthin-Oxidase, Lactase, Dextranase etc. |
| CM-Cellulose, AE-Cellulose | Carbodiimide method | Peroxidase, etc. |
| Nitrocellulose-Membranes | Membrane inclusion | Glucose-Oxidaae Peroxidase, etc. |
| Bromcyan-activated Cellulose Membranes | Membrane inclusion Bromcyan activation | Lactase, Trypsin etc. |

The columns in Table 1 can be expanded with respect to further cellulose derivatives, for example, cellulose carbonate chloracetylcellulose, bromacetylcellulose, etc., and also with reference to further biocompounds, for example, further enzyme species, NAD- and pyridoxal-phosphate coenzyme, vitamin $B_{12}$, immunoproteins and the like.

In the forefront of the examples given, are preparative or analytic, e.g. chromatographic, applications in which the carrier compounds with receptor compounds or enzymes will depend only on the loading density and without special molecular geometric considerations.

With respect to the functional requirements, for example with the enzyme immobilization process, very different scales apply depending upon the field of use. Target criteria of an effective enzyme immobilization are a precise folding of the proteins, a free substrate accessibility of the active center, an effective product recovery, carrier fixation on the enzyme-molecular periphery, a high enzyme loading density per unit of carrier matrix surface and in the case of use as a sensor, a carrier matrix with signal structure features which affords a maximum optical or electronic transfer signal transduction.

The use of reagent solid phases in (bio) chemical sensor technology requires that, for each sensor development for a respective analyte, a new structure optimization based upon the aforestated criteria; the sensor solution for one analyte then can hardly be used for other analytes without further translation. This drawback in the state of development in the (bio) chemical sensor field makes the use of many scientifically determined sensor developments limited in practice, because there is a significant gap between the requirements of the sensor user and the generally limited functional stability and cross sensitivity of the sensors.

A solution of this problem was expected from sensor transducers of a "measurement-tailored" supermolecular structure with improved signal transmission characteristics. Such a transducer is known, for example, from enzyme electrode developments, using polymeric carrier compounds with so-called electron mediator structures, e.g. ferrocene derivatives, and immobilized enzymes, for improved signal transduction by reduction of the electron transition "barriers", and the measurement electrode (see B. Frew, J. E. and Hill, H. A. O. (1987); Electrochemical Biosensors, Anal. Chem. 59, 933A; Frew, J. E. and Hill, H. A. O. (1987): Electron-transfer-Biosensors, Phil. Trans. R. Soc. B316, 95; Bockris, J. O'M. and Khan, S. U. M. (Ed.): Surface Electrochemistry—A Molecular Level Approach, Plenum Press, 1993).

Significantly more complex supermolecular structures are required in the case of (bio) chemical glass fiber sensor transducers. The higher complexity is based upon the fact that an enzyme protein which possesses the requisite function and in most cases in addition, a further structure component, for example, an indicator structure, must be provided in a well-defined molecularly geometric positioning of the structures relative to one another on the polymer or macromolecular carrier matrix. Exceptions in which an additional signal structure is not required form analyte recognition structures wherein the analyte recognition and the optical signal transfer are inherent in the structure; for these up to now there have however been few examples.

In the field of glass fiber sensor technology there have already been reagent solid phases used which have cellulose derivatives as carrier compounds, on which pH indicators have been immobilized via vinylsulfonyl groups as couplers (Weigl, B. H. et al. (1993): Robust Carbon Dioxidoptode Based on a Covalently Immobilized pH-Indicator, SPIE-Vol. 2068, 2). In addition, the use of cellulose acetate membranes in combination with pH indicators has been described (Sansubrino, A. and Mascini, M. (1994): Development of an Optical Fiber Sensor for Ammonia, Urea, Urease and IgG, Biosens. Bioelectron. 9, 207).

The development of (bio) chemical glass fiber sensors is of special interest because of their capacity for integration, the possibility of a high degree of miniaturization and further advantageous characteristics, they are well characterized for use in analytic micro systems, for example, in vivo diagnostics in medicine. A substantial prerequisite which, up to now has been deficient, has been sensor transducers with improved signal transmission characteristics on the basis of corresponding "measurement tailored" supermolecular architectures which can be fabricated from readily accessible and least expensive starting materials, using the simplest possible process.

OBJECTS OF THE INVENTION

It is an object of the invention to prepare new (bio) chemical reagent solid phases whose structure allows the widest possible range of modification possibilities and thus a high degree of versatility, especially as analyte sensitive solid phases in sensor technology. It is also an object of the invention to provide a simple process for producing such reagent solid phases.

SUMMARY OF THE INVENTION

These objects are attained in accordance with the invention with a polymeric macromolecular, $NH_2$-containing carrier compound with coupling structures covalently bonded via $NH_2$ groups, whereby the coupling structures are comprised of ascorbic acid or dehydroascorbic acid or a compound structurally similar to one of these substances. The coupling structures are, moreover, linked with a receptor compound and/or indicator compound so that these are coupled to or immobilized on the carrier. As substances structurally similar to ascorbic acid or dehydroascorbic acid, mention may be made especially of L-2,3-diketogulonic acid or a derivative thereof. There are compounds which can be included as structurally similar compounds which include for example compounds with at least two keto groups, like acetylacetone.

An alternative solution according to the invention for the aforementioned objects are (bio) chemical reagent solid phases of the described type in which the carrier compound is a cellulose derivative of the following formula I:

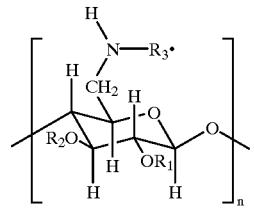

in which $R_1$. $R_2$=H
or $R_1$=H, $R_2$=substituent with a degree of substitution ≤ 1
or $R_1$ is a substituent of degree of substitution ≤ 1, $R_2$=H
or $R_1$, $R_2$=a substituent with a degree of substitution ≤ 2
and $R_3$ is an aromatic substituent which contains at least one free amino group and a degree of substitution ≤ 1.

The residue $R_3$ is preferably an amino residue of the formula

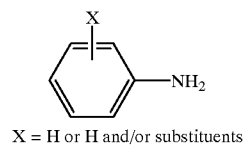

X = H or H and/or substituents

As the amine or amine residue, compounds can be used for example with the following structural formulas:

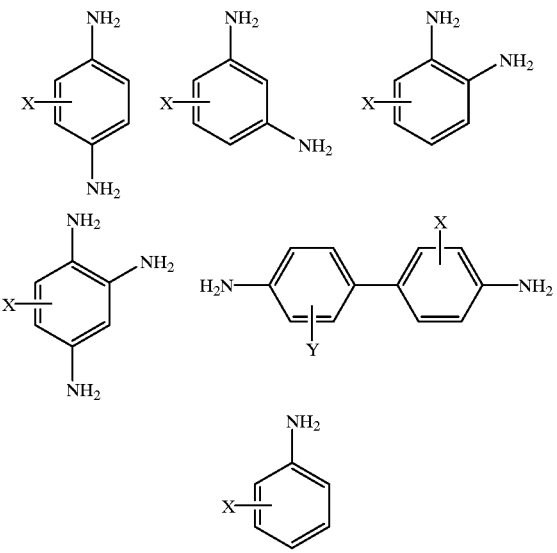

X = H or H and/or substituents
Y = H or H and/or substituents

According to the formula I, the basic framework is either cellulose ($R_1$, $R_2$=H) or a cellulose derivative. In case, a cellulose derivative basic framework is provided, the substituent in the $R_1$ position and/or $R_2$ position, is an alkyl, preferably $CH_3$, or acyl, preferably acetyl, or a tosyl residue or a tresyl residue. The substituent in the named position can be exclusively a substituent of the named type or in the $R_1$ position and/or $R_2$ position can be within a macromolecule which can include different substituents of the named type.

The (bio) chemical reagent solid phase containing such a carrier compound can be used especially as the analyte sensitive solid phase in the sensor technology for which it is highly suitable since the carrier compounds have, above all, redox-chromogenic characteristics which, by multiple structural alterations by known coupling reactions to the free aromatic $NH_2$ groups, provide a wide range of chromogenic modification possibilities. Because of the characteristics, supermolecular structures can be formed which signal the "recognition" of the analyte (i.e. when the compound having an affinity to the receptor enters into an exchange therewith) which is optically "signalled" or "signals" by electron transfer.

The supermolecular "basic" structure according to the invention enables the following broadening or modification possibilities.

Figure 1:
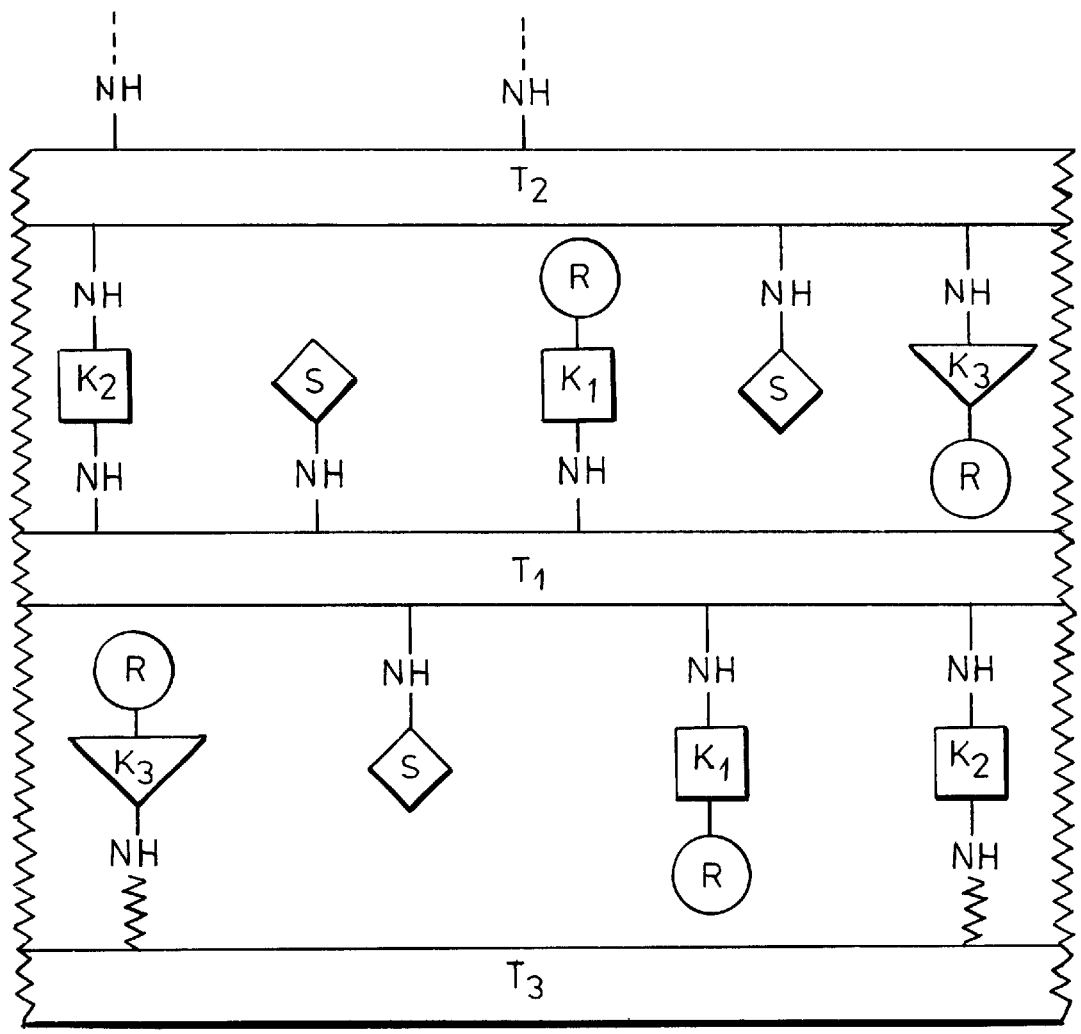
FIG. 1 shows a carrier matrix $T_1$ linked via $NH_2$ groups with coupling structures K, whereby the coupling structures of the invention are illustrated as the squares $K_1$ and $K_2$.

At least one coupling structure of at least one further polymeric and/or macromolecular $NH_2$-containing carrier compound can be linked to it in accordance with the "sandwich principle" whereby on $NH_2$ groups of each, further carrier compounds, additional receptor compounds are fixed by further coupling structures. For illustration, two possible embodiments of a biochemical reagent solid phase have been schematically illustrated in FIG. 1 and in FIG. 2 and are described in greater detail in the following.

In illustration, a carrier matrix $T_1$ is linked via $NH_2$ groups with coupling structures K, whereby the coupling structures of the invention are illustrated as the squares $K_1$ and $K_2$.

On the carrier $T_1$, via coupling structures $K_1$, receptor compounds R are immobilized. Further coupling structures $K_2$ of the carrier $T_1$ are linked by $NH_2$ with the carrier compounds $T_2$ and $T_3$ in accordance with the "sandwich principle." Further $NH_2$ groups link coupling structures $K_3$ immobilizing further receptors to the carriers $T_2$ and $T_3$. The coupling structures $K_3$ can also be coupling compounds in accordance with the invention, or they can be other $NH_2$ reactive homobifunctional or heterobifunctional or multifunctional coupling compounds or so-called cross linkers.

For example, the following can be used:
cyanurchloride or
dialdehyde, like glutaricdialdehyde, or
diketone, like acetylacetone, or
compounds which have at least one aldehyde and at least one keto group containing compound or compounds with more than two aldehyde groups and/or keto groups, or
p-quinoide compounds, like benzoquinone, or
aromatic disulfone acid-dichloride, like benzol-1,4-disulfone acid-dichloride, or
activated diester compounds like bis-succinimidyl and/or bis-maleimidyl-dicarboxylic acid diester, or
bis-diazo compounds like bis-diazobenzidine, or
photoactive cross linkers, like p-azido-phenylglyoxal, p-azido-phenylisothiocyanate, p-azido-phenacylbromide, 4,4'-diazidostilbene-2,2'-disulfonic acid-disodium salt, or
the coupling is effected by means of a diazotizing reaction, starting from free aromatic $NH_2$ groups, with the carrier compound.

The carrier $T_1$ is preferably a cellulose derivative as described previously of the Formula I or another cellulose derivative with aromatic substances with at least one free amino group. For example cellulose derivatives like p-aminophenyl cellulose, p-aminobenzyl cellulose, or p-phenylenediamine-substituted cellulose derivatives other than the 1,4-phenylendiamine cellulose derivatives of the Formula I.

The carrier matrix $T_1$ and/or $T_2$ can, either be comprised also from $NH_2$-containing polymers, like polyaminopolystyrene, polyacrylamide derivatives or macromolecular compounds other than cellulose derivatives, for example, proteins, like collagen.

Further carrier compounds linked according to the sandwich principle are either identical with the carrier $T_1$ or different from it. Thus, for example $T_3$ can be a (transducer) substrate, like aminosilanized, e.g. aminopropyl activated, porous glass or a fiber optics or a silicon-nitride substrate.

The coupling structures according to the invention enable then a frequently desirable covalent fixation of the analyte sensitive layer on such a substrate.

Linkages with further polymer or macromolecular $NH_2$-containing carrier compounds as have been shown generally in FIG. 1 as described above are then also a preferred modification of reagent solid phases, when the carrier compound according to the invention is a cellulose derivative of the Formula I and as coupling structures others than those according to the invention are provided. As coupling structures in this case, preferably disulfonic acid amides come under consideration.

Reagent solid phases that contain a cellulose derivative of the Formula I as the carrier compound are preferably linked via $NH_2$ groups of the carrier compound with oxidative coupling-favoring compounds. As the oxidative coupling-favoring compounds there are such coupling compounds as are known from color photography or the patent literature for test strip development and operate based upon oxidative coupling reactions (peroxidase-catalyzed) with N,N-disubstituted p-phenylendiamines. The above-mentioned reagent solid phases according to the invention contain as oxidative coupling favoring compounds preferably phenol or naphthol or derivatives thereof.

Aromatic $NH_2$ groups of the cellulose derivatives under oxidative coupling conditions are transformed into a quinone-analog structure. This is especially of advantage in broad modification or use possibilities in the redox-chromogenic characteristics, especially, the light absorption and redox potential characteristics and their pH dependency. If oxidative coupling structures in addition are linked with receptor compounds, additionally via a supermolecular geometrical coupling with receptor structures with analyte affinity the redox chromogeneric coupling structure has an advantageous effectiveness. By use of cellulose derivatives of the Formula I as carrier compounds in reagent-solid phases, the coupling structure with an oxidative coupling-favoring compound is advantageous. Such reagent solid phases are, for example, usable especially for analytic purposes in redox systems, especially hydrogen peroxide generating and hydrogen peroxide utilizing enzyme-substrate systems or quinoprotein-enzyme substrate systems.

The receptor compounds which are considered are oxido-reductase enzymes, immunoproteins with oxidase markers or peroxidase markers, redox-metal ion chelate compounds, preferably oxidoreductase enzymes, especially flavoprotein oxidase and/or peroxidase enzymes, when the carrier compound is a cellulose derivative, especially of the Formula I.

Such regent solid phases are superior for the use in (bio) chemical sensor transducer development, preferably for analytes in the field of medicinal diagnostics, environmental analysis, food analysis or biotechnical process control or for other (bio)chemical analytic requirements or in preparative activities, especially in biotechnology or in (bio) chemical practice.

It is however also conceivable to use as receptor compounds only cofactors of enzymes, like FAD, NAD or the like because in combination with the corresponding enzyme proteins and with the use of corresponding supermolecular architecture variants according to FIG. 1, a multiple application, especially with respect to the fields of analysis is possible in enzyme technology or biotechnology.

In the use of the reagent-solid phases, according to the invention, the receptor compounds engage with compounds having an affinity for the receptor in a reciprocal action. This is often associated with the conversion reaction which can be measured by an indicator structure or signal structure S (compare in FIG. 1) positioned neighboringly in the super-molecular structure, for example by a change in the optical or electron transfer characteristics of the reagent solid phases as a function of the concentration of the compound having such affinity. The invention also is a simplified process for producing (bio) chemical reagent solid phases in which one reacts at least one $NH_2$-containing carrier compound with a coupling compound and then with a $NH_2$ containing receptor compound, whereby the coupling compound according to the invention is ascorbic acid, dehydroascorbic acid or a substance structurally similar thereto. It has been found surprisingly that a solution of ascorbic acid, dehydroascorbic acid or 2,3-diketogulonic acid or structurally similar compounds act as bifunctional reagents with covalent coupling or immobilization of $NH_2$-containing compounds.

The production of (bio) chemical reagent-solid phases can have a variety of pathways according to the invention, depending upon the number and type or structure of the (solid phase) layer sequence according to the succession of $NH_2$-containing polymers or macromolecular carrier compounds, receptor compounds and/or indicator structures or signal structures as well as with respect to the type of coupling reactions.

If, for example, according to the process of the invention, a plurality of $NH_2$-containing compounds are linked in accordance with the above-described "sandwich-principle", one can dissolve the $NH_2$-reactive coupling compound, for example ascorbic acid, preferably in dimethylacetamide, dimethylsulfoxide or tetrahydrofuran and contact the same with the $NH_2$-containing carrier compound at room temperature, if required, at +4° C. After this contact time depending upon the reactivity of the reaction partners lying between several minutes and several hours, unreacted coupling compound is washed with bidistilled water or alcohol. Then the functionalized carrier compound is treated with the $NH_2$-containing compound to be coupled therewith, for example a receptor compound and/or cellulose derivatives as aromatic $NH_2$ substituents especially of the above-mentioned Formula I. For this treatment, the receptor compound as a rule is in the form of an aqueous solution and the cellulose derivative especially in dimethylacetamide solution.

Thereafter, with use of the aforementioned cellulose derivative as carrier compound, an additional reaction can be carried out with a reducing agent, especially sodium-cyanoborhydride ($NaBH_3CN$); alternatively a new reaction can be effected with one of the mentioned coupling compounds and/or a treatment with an oxidative coupling favoring compound, especially with phenol, naphthol or derivatives thereof. The phenol derivative can preferably be an aqueous (buffer) solution (pH 7 to pH 8) of 2,4,6-tribromo-3-hydroxy-benzoic acid, hydrogen peroxide and peroxidase enzyme as catalyst. The result is an oxidative coupling reaction to the free aromatic $NH_2$ groups of the 1,4-phenylendiamine residue at room temperature or, if required, at +4° C. in 10 to 60 minutes as is known from biochemical peroxidase catalyzed analysis.

Thereafter the solid phase which now contains the blue colored above-mentioned phenol derivative with its quinone analog structure has an oxidative coupling product, is washed with water. Then, depending upon the use to which the reagent solid phase is to be put, it can be employed directly or anew reacted with an $NH_2$-containing compound to effect coupling reaction to the quinone analog structure. The $NH_2$-containing compound can be a carrier compound, preferably a cellulose derivative according to Formula I, and/or a receptor compound, preferably an oxidoreductase enzyme, especially a flavoprotein oxidase in a concentration of 10 to 1000 U/ml of aqueous solution, The reagent solid phase can then be used, depending upon the application or anew subjected to reaction with known $NH_2$ reactive coupling compounds and thereafter with a carrier compound and/or a receptor compound and/or an indicator compound, preferably a redox chromogen, like an oxidative coupling product or a redox-metal ion-chelate compound or any such compound according to the invention, and if desired, reacted a number of times with such compounds in order to produce a (bio) chemical reagent solid phase for the above-described purposes.

The important advantage of the process according to the invention is that aside from its simplicity is the mild reaction conditions which are required, especially with use as a cellulose derivative according to Formula I, and the multiple modification possibilities with respect to the use application and, indeed, because of the high variability of the coupling reactions and the multiplicity of layer sequences with respect to cellulose derivatives or carrier compounds, receptor compounds and/or indicator compounds which can achieve a high loading density with recognition and signal structures and their matching to the application. It has also been found to be advantageous that the ascorbic acid or dehydroascorbic acid used for the coupling reactions according to the invention are readily available and nontoxic.

The compounds of the Formula (I) are prepared by reacting an aromatic diamine or an aromatic triamine of the Formula

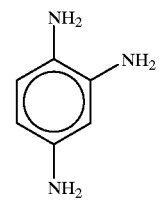

with a tosyl-(=toluene sulfonyl-) or tresyl cellulose of the Formula Ia

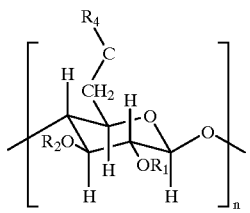

Ia wherein $R_1, R_2 = H$ or $R_1 + H, R_2 =$ alkyl, acyl, tosyl or tresyl with a substitution degree $\leq 1$ or $R^1, R_2 =$ alkyl, acyl, tosyl or tresyl with a substitution degree of $\leq 2$ and $R_4$ is a tosyl or tresyl residue with a substitution degree $\leq 1$.

Surprisingly it has been found that according to the substitution of the invention, corresponding cellulose derivatives can be produced in a single synthesis step. Thereby the tosyl and tresyl residues ($R_4$) existing at the C-6 of the generic structural formula of the cellulose (at $R_1$, $R_2 = H$), respectively of the cellulose derivative (at $R_1$ and/or $R_2 =$ substituent) are replaced directly by the aromatic amine. The residue $R_4$ existing on the C-6 of the generic structural formula can be exclusively a tosyl or tresyl residue, but it is also possible that both residues are represented in $R_4$-position within the macromolecule.

In the process of the invention preferably a phenyl diamine, respectively 1,4-phenyl diamine, is used as an aromatic diamine. It is possible to use aromatic diamines, for instance compounds with the following structural formulas:

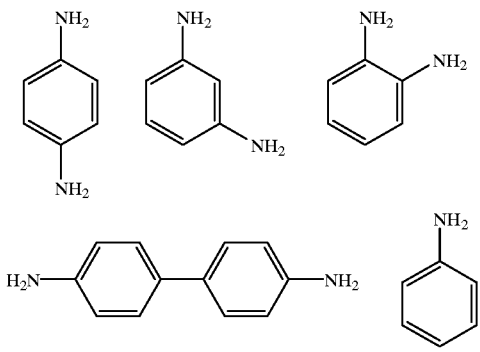

The compound with the following structural formula can be used as aromatic triamine:

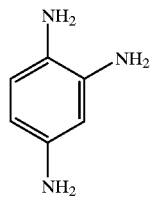

For the substitution such tosyl or tresyl cellulose derivatives are used, wherein the substituent in the $R_1$ and/or $R_2$ position of the generic structural formula is an alkyl, preferably $CH_3$, or an acyl, preferably acetyl, or a (further) tosyl or tresyl residue. Thereby here too the substituent in the $R_1$ and/or $R_2$ position can be a substituent of the mentioned kind, or different substituents of the mentioned kind can be represented in $R_1$ and/or $R_2$ positions within a macromolecule.

The synthesis according to the invention takes place in a known suitable solvent, such dimethylformamide or dimethylacetamide, preferably in dimethylsulfoxide (DMSO). The reaction can be performed in the presence of an organic base, whereby as a base pyridine or triethylamine are especially suitable. When using triethylamine, preferably 0.15 parts by weight of this base are used for the synthesis of the invention, whereby a triethylamine layer covers the reaction mix. The selection of the reaction temperature and duration follows the selection of further reaction conditions: If for instance the reaction is performed without the addition of a base, for the substitution of the invention particularly a temperature of 100° C. and a duration of 5 hours are suitable; but if the reaction takes place with triethylamine, at a temperature of 100° C. a reaction time of 3 hours is sufficient. Generally optimizing tests have shown that an optimal substitution takes place at a temperature of 80° C. to 120° C. over a time period of 1 to 10 hours.

EMBODIMENT EXAMPLES

Synthesis Example I

A mixture of 0.5 g tosylcellulose (DS=2.3) and 1 g phenylenediamine is dissolved in 5 ml DMSO and the solution is reacted 2.5 ml triethylamine. The reaction mixture is strongly agitated from time to time at a temperature of 100° C. over a time of 3 hours and allowed to rest during the pauses between stirring. When the reaction mixture is at rest a cover layer of excess triethylamine is formed, which protects the mixture against autoxidation. Towards the end of the reaction time, the clear solution assumes a brownish coloring. After the mixture is cooled, the white-colored reaction product is precipitated in ethanol, centrifugated and washed with ethanol for about 5 times. The solid substance in freshly precipitated state is soluble in THF, DMSO or DMAC. For further processing preferably DMAC solutions of the p-phenylenediamine cellulose derivative are used.

Synthesis Example 2

A mixture of 100 mg tosylcellulose (DS=2.3) and 150 mg p-phenylenediamine is dissolved in 1 ml DMSO and the solution is heated to 100° C. while being stirred. During a reaction time of 8 hours the mixture is colored in a dark brown. After cooling a slightly colored reaction product is precipitated in ethanol. The solid substance is centrifuged, washed for about 5 times with ethanol and subsequently dissolved in DMAC.

Synthesis Example 3

A mixture of 200 ml 2,3-di-methyl-6-tosylcellulose and 300 mg p-phenylenediamine is dissolved in DMAC and the solution is reacted with triethylamine. The reaction mixture is left to rest for a total time period of 3 hours at a temperature at first of 80° C. and at the end for approximately 30 min at 100° C. Afterwards the brown reaction mixture is cooled to room temperature and a solid substance with a slight brown coloring is precipitated in ethanol. The solid substance is centrifuged, washed for about 5 times in ethanol and subsequently dissolved in DMAC.

Synthesis Example 4

A mixture of 300 mg tosylcellulose (DS=2.0) and 300 mg p-phenylenediamine is dissolved in 2 ml DMSO and the solution is reacted with 500 μl pyridine. The reaction mixture is heated to 80° C. for a period of 3 hours and subsequently left to rest for 30 minutes at approximately 120° C. After the cooling of the reaction mixture to room temperature, a brown-colored reaction product is precipitated in ethanol, centrifuged and the solid brownish substance is washed for about 5 times in ethanol. Subsequently the solid substance is dissolved in DMAC.

EXAMPLES

1.1 Production of Solid Phases According to the Invention

A) Layers of 1,4-phenylenediamine-cellulosic Derivatives is Preparation of the Layers Glass rods (d=1,3 mm) are immersed in a viscous solution of 1,4-phenylenediamine-cellulosic derivatives (see patent application No. DE-196 00 929 "New Aromatic Amine-Cellulose Derivatives and Process for Their Manufacture") in DMAc (about 4mm immersion height) for a short time. They are withdrawn after a short time (1 to 2 minutes) and dried for 5 to 10 hours in air. The result is a solid and transparent layer on the glass rods which is used in the following synthesis examples.

A1) Glucose Sensitive Cellulose Solid Phase (Optical Signal at 550 nm)

Functionalization of the Solid Phase of Means of Ascorbic Acid Solution

A glass rod prepared by the process technique A is immersed, when the cellulose derivative layer in a solution of 1 g ascorbic acid in 2,5 ml DMAc, removed after a brief effective duration (about 1 minute). and then dried for 4 to 5 hours in air. The solid phase which has in the meantime become colored purple, is then washed with bidistilled water about 5 times and can be used to immobilize a receptor compound:

Enzyme-Immobilization on the Solid Phase

The functionalized solid phase is immersed in an enzyme solution of glucose oxidase (GOD) in bidistilled water (40 U GOD/ml water) for a period of 8 to 15 hours at 4° C.

The purple colored solid phase is then washed with bidistilled water 3 to 5 times and then treated briefly (about 1 minute) with an aqueous ascorbic acid solution to transform the solid phase into the leuko-form. The solid phase responds at a wavelength of 540 . . . 560 nm to glucose concentrations.

A2) Glutamate-Sensitive Cellulose Solid Phase (Optical Signal at 550 nm)

Following the procedure A1) functionalized solid phase is immersed in an enzyme solution of glutamate-oxidase (GlOD) in bidistilled water (15 U GlOD/ml water) for a period of 8 to 15 hours at 4° C. Then the purple colored solid phase is washed about 5 times with bidistilled water and then treated with an aqueous ascorbic acid solution briefly (about 1 minute) to transform the solid phase into the leuko form. The solid phase responds at a wavelength of 540 . . . 560 nm to glutamate concentrations.

A3) Glucose Sensitive Solid Base (Optical Signal at 660 nm)

A glucose-sensitive solid phase prepared in accordance with the procedure Al is treated with a solution of 2 ml of a buffer solution (pH 8), 1 ml of a 7.5 m molar 2,4,6-tribromo-3-hydroxybenzoic acid solution in distilled water, 100 μl of a 100 m molar $H_2O_2$ solution and 50 μl of a peroxidase (POD) solution in bidistilled water (150 U POD/ml). After 30 to 60 minutes of standing at room temperature the solid phase which has become blue colored in the meantime, is removed from the solution, washed with bidistilled water about 5 times and then briefly (about 1 minute) treated with an aqueous ascorbic acid solution and again washed about 5 times with bidistilled water. The solid phase responds to glucose concentrations at a wavelength of 650 . . . 670 nm.

A4) Glucose-Sensitive Cellulose Solid Phase (Optical Signal at 660 nm)

A coated glass rod prepared by the procedure A) is briefly (about 2 seconds) immersed in DMAc and then washed about 3 times with bidistilled water. The solid phase is then treated with a solution as described in Example A3). After about 30 minutes, the dark blue colored solid phase is washed about 5 times with bidistilled water and treated with a GOD solution as described in Example A1) or worked up therewith. The solid phase responds, after conversion to the leuko form by means of ascorbic acid solution (compare under A3) to glucose concentration at a wavelength of 660 nm.

A5) Glucose-Sensitive Cellulose Solid Phase Optical Signal at 550 nm)

Functionalization of the Solid Phase by benzene- 1, 3-disulfonic Acid Dichloride A coated glass rod prepared as by the procedure A) is immersed in a solution of 500 mg benzene-1,3-disulfonic acid dichloride in 2 ml DMAc, is removed after about 1 minute and then dried for about 5 hours in air. Then the solid phase which has in the meantime colored red, is washed about 5 times alternately with ethanol and bidistilled water and, thereafter treated or processed with an enzyme solution, e.g. GOD solution as described in Example A1). The solid phase response, in the case of GOIOD as the example of the enzyme, to glucose concentration at a wavelength of 550 nm.

1.2 Example of a Solid Phase According to the Invention

Figure 2:
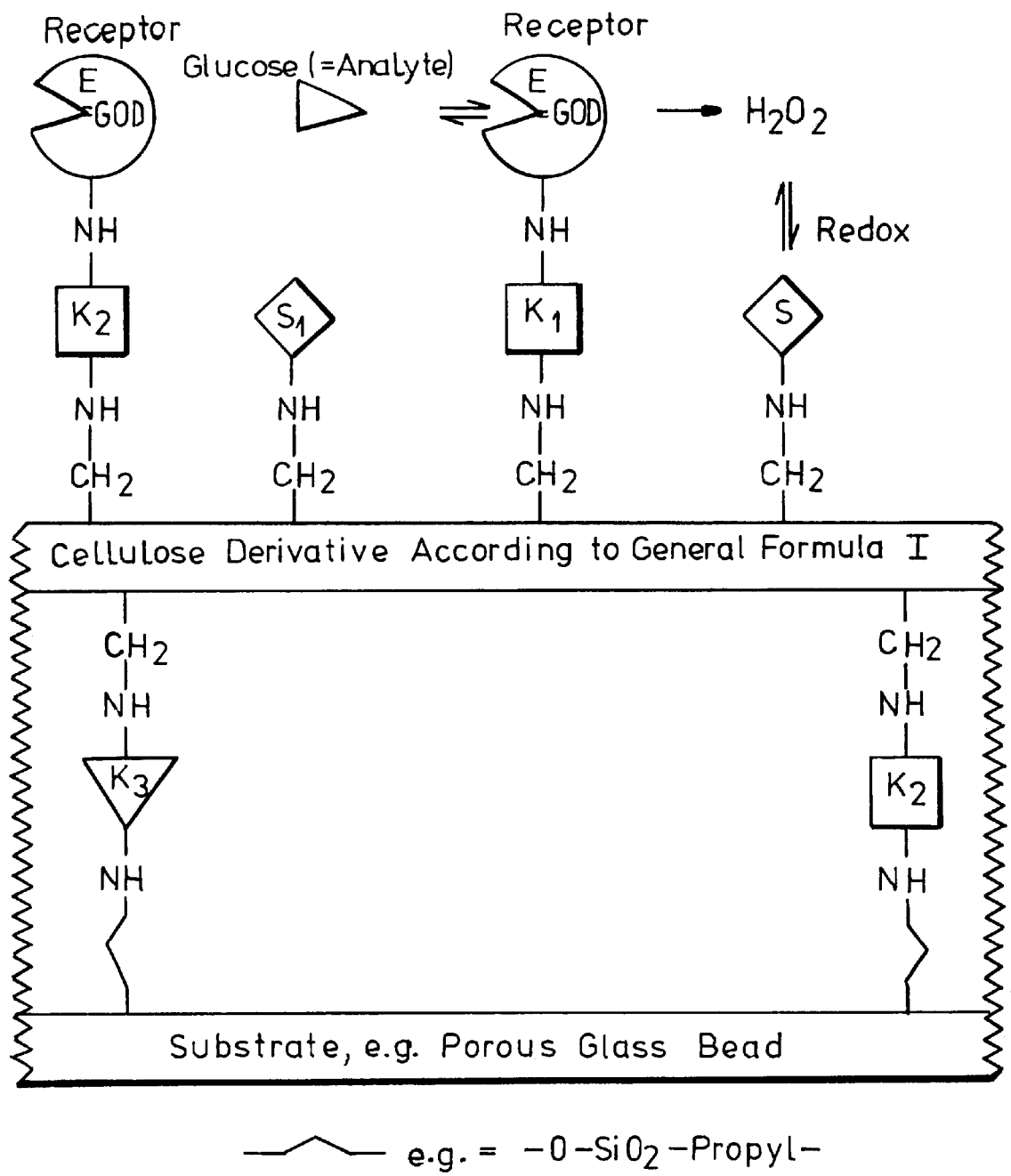
FIG. 2 shows a chemical reagent solid phase containing as a substrate aminopropyl activated porous glass beads coated with the polyaminocellulose of the Formula (I) which is linked by ascorbic acid as coupling structures $K_1$ and $K_2$ via 1,4-phenylenediamine residues and the quinone-like coupling structure $K_1$ and additionally via ascorbic acid $K_2$ glucose oxidase is immobilized as a receptor.

An example of a solid phase according to the invention is illustrated in FIG. 2 and is described more fully below:

The (bio) chemical reagent solid phase according to FIG. 2 contains as a substrate, aminopropyl activated porous glass which is linked by ascorbic acid as coupling structures $K_2$ and $K_3$ via 1,4-phenylenediamin residue and the quinone coupling structure $K_1$ and additionally via ascorbic acid $K_2$, glucose oxidase (GOD) is immobilized as a receptor. Free 1,4-phenylenediamin residue S, present as a (redox-) indicator or signal structure of the formula

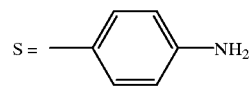

and additionally the compound has a coupling structure $S_1$ formed by ascorbic acid and which is coupled starting from 2,4,6-tribromo-3-hydroxybenzoic acid as the coupling-favoring compound and is not provided with GOD. $K_1$ can be a redox chromogen.

Glucose (=analyte) is transformed as an enzyme structure with affinity into a corresponding product with generation of hydrogen peroxide. The resulting $H_2O_2$ reacts with a supermolecular geometric neighboring leuko form of the redox indicator structure with the formation of the chromogeneric oxidized form of S. The result is a change in the spectrophotometric characteristics of the reagent solid phase which is measurable via an optical waveguide, such an optical fiber, by the use of an optical detection, for example by means of a PIN-diode.

What is claimed is:

1. A solid phase reagent support which comprises:
   (a) a solid phase carrier having a multiplicity of $NH_2$ functional groups comprising a cellulose compound having phenyl or biphenyl substituents which contain at least one free amino group directly bonded to said substituents;
   (b) a coupling compound comprising ascorbic acid, dehydroascorbic acid or a diketo compound selected from the group consisting of an L-2,3-diketogulonic acid and an acetylacetone covalently bonded to an $NH_2$ group of the solid phase cellulose-containing carrier; and
   (c) an oxidoreductase coupled to the solid phase carrier through the coupling compound.

2. The solid phase reagent support defined in claim 1 wherein the cellulose compound is a compound of the Formula (I)

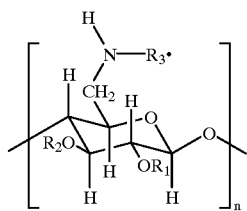

I in which $R_1$ and $R_2$ are each H,
   or $R_1$ is H and $R_2$ is an alkyl or acyl substituent with a degree of substitution$\leq 1$ or $R_1$ is an alkyl or acyl substituent with a degree of substitution$\leq 1$, and $R_2$ is H,
   or $R_1$ and $R_2$ are each a substituent with a degree of substitution$\leq 2$ and $R_3$ is a phenyl or biphenyl substituent containing at least one free amino group directly bonded to the substituent and having a substitution degree$\leq 1$.

3. The solid phase reagent support defined in claim 2 wherein the substituent $R_1$ and/or $R_2$ is a methyl group or is an acyl group selected from the group consisting of acetyl, tosyl and tresyl.

4. The solid phase reagent support defined in claim 1 wherein the cellulose compound having phenyl or biphenyl substituents which contain at least one free amino group directly bonded to said substituents is a 1,4-phenylene-diamino cellulose.

5. A process for preparing a solid phase reagent support which comprises:
   (a) a solid phase carrier having a multiplicity of $NH_2$ functional groups comprising a cellulose compound having phenyl or biphenyl substituents which contain at least one free amino group directly bonded to said substituents;
   (b) a coupling compound comprising ascorbic acid, dehydroascorbic acid or a diketo compound selected from the group consisting of an L-2,3-diketogulonic acid and an acetylacetone, covalently bonded to an $NH_2$ group of the solid phase carrier; and
   (c) an oxidoreductase coupled to the solid phase carrier through the coupling compound, which comprises the steps of:
      (1) reacting the cellulose compound having phenyl or biphenyl substituents which contain at least one free amino group directly bonded to said substituents with a coupling compound comprising ascorbic acid, dehydroascorbic acid or a diketo compound selected from the group consisting of an L-2,3-diketogulonic acid and an acetylacetone, to covalently bond the coupling compound to the $NH_2$ group of the solid phase carrier; and
      (2) reacting the solid phase carrier containing the coupling compound covalently bonded thereto with the oxidoreductase to couple the oxidoreductase to the solid phase carrier through the coupling compound.

6. The process for preparing the solid phase reagent support defined in claim 5 wherein as the cellulose compound with phenyl or biphenyl substituents, a compound of the Formula (I) is used

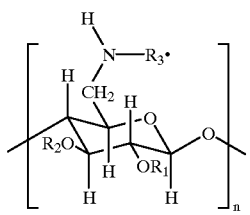

I in which $R_1$ and $R_2$ are each H,
   or $R^1$ is H and $R_2$ is an alkyl or acyl substituent with a degree of substitution$\leq 1$ or $R_1$ is an alkyl or acyl substituent with a degree of substitution$\leq 1$, and $R_2$ is H,
   or $R_1$ and $R_2$ are each a substituent with a degree of substitution$\leq 2$ and $R_3$ is a phenyl or biphenyl substituent containing at least one free amino group directly bonded to the substituent and having a substitution degree$\leq 1$.

7. The process for preparing the solid phase reagent support defined in claim 6 wherein the solid phase reagent support comprises as the cellulose compound a 1,4-phenylene-diamino cellulose.

8. A solid phase support system for a reagent which comprises:
   (a) a solid phase carrier having a multiplicity of $NH_2$ functional groups comprising a cellulose compound having phenyl or biphenyl substituents which contain at least one free amino group directly bonded to said substituents; and
   (b) a coupling compound comprising ascorbic acid, dehydroascorbic acid or a diketo compound selected from the group consisting of an L-2,3-diketogulonic acid and an acetylacetone, covalently bonded to an $NH_2$ group of the solid phase carrier and capable of coupling to an oxidoreductase.

9. The solid phase reagent support defined in claim 1 wherein the coupling compound is ascorbic acid and the oxidoreductase is glucose oxidase.

* * * * *